(12) United States Patent
Hart et al.

(10) Patent No.: US 12,397,146 B2
(45) Date of Patent: Aug. 26, 2025

(54) FLEXIBLE TIP FOR TRANSVALVULAR CIRCULATORY SUPPORT DEVICE

(71) Applicant: Boston Scientific Scimed Inc., Maple Grove, MN (US)

(72) Inventors: Matthew Hart, Maple Grove, MN (US); Thomas P. Jancaric, Maple Grove, MN (US); Umang Anand, Plymouth, MN (US); Matthew N. Frost, New Brighton, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 637 days.

(21) Appl. No.: 17/720,663

(22) Filed: Apr. 14, 2022

(65) Prior Publication Data
US 2022/0331577 A1    Oct. 20, 2022

Related U.S. Application Data

(60) Provisional application No. 63/174,810, filed on Apr. 14, 2021.

(51) Int. Cl.
*A61M 60/13* (2021.01)
*A61M 25/00* (2006.01)
*A61M 60/174* (2021.01)

(52) U.S. Cl.
CPC .......... *A61M 60/13* (2021.01); *A61M 60/174* (2021.01); *A61M 25/0074* (2013.01)

(58) Field of Classification Search
None
See application file for complete search history.

(56) References Cited

U.S. PATENT DOCUMENTS

| | | |
|---|---|---|
| 5,527,159 A | 6/1996 | Bozeman, Jr. et al. |
| 5,692,882 A | 12/1997 | Bozeman, Jr. et al. |
| 5,947,892 A | 9/1999 | Benkowski et al. |
| 6,135,729 A | 10/2000 | Aber |
| 6,139,487 A | 10/2000 | Siess |
| 6,176,822 B1 | 1/2001 | Nix et al. |
| 6,974,436 B1 | 12/2005 | Aboul-Hosn et al. |
| 7,841,976 B2 | 11/2010 | McBride et al. |
| 7,927,068 B2 | 4/2011 | McBride et al. |

(Continued)

FOREIGN PATENT DOCUMENTS

| | | |
|---|---|---|
| EP | 0847767 B1 | 2/2005 |
| EP | 2301598 B1 | 7/2017 |
| EP | 3352808 B1 | 9/2023 |

OTHER PUBLICATIONS

US 9,607,007, 06/2015, Tanner et al. (withdrawn)

(Continued)

*Primary Examiner* — Carl H Layno
*Assistant Examiner* — Bryan McAllister Lee
(74) *Attorney, Agent, or Firm* — Seager, Tufte & Wickhem LLP

(57) ABSTRACT

Various aspects of the present disclosure are directed towards apparatuses, systems, and methods that may include a blood pump. The blood pump may include a flexible distal tip having a distal end segment, an intermediate segment, and a proximal segment, each segment having various shapes and/or hardness. The blood pump may include a cannula and a can element coupling the flexible distal tip to the cannula.

20 Claims, 7 Drawing Sheets

(56) References Cited

U.S. PATENT DOCUMENTS

| | | |
|---|---|---|
| 7,972,122 B2 | 7/2011 | LaRose et al. |
| 8,376,707 B2 | 2/2013 | McBride et al. |
| 8,591,393 B2 | 11/2013 | Walters et al. |
| 8,597,170 B2 | 12/2013 | Walters et al. |
| 8,617,239 B2 | 12/2013 | Reitan |
| 8,684,904 B2 | 4/2014 | Campbell et al. |
| 8,721,517 B2 | 5/2014 | Zeng et al. |
| 8,992,163 B2 | 3/2015 | McBride et al. |
| 9,072,825 B2 | 7/2015 | Pfeffer et al. |
| 9,138,518 B2 | 9/2015 | Campbell et al. |
| 9,162,017 B2 | 10/2015 | Evans et al. |
| 9,308,302 B2 | 4/2016 | Zeng |
| 9,308,304 B2 | 4/2016 | Peters et al. |
| 9,327,067 B2 | 5/2016 | Zeng et al. |
| 9,364,592 B2 | 6/2016 | McBride et al. |
| 9,364,593 B2 | 6/2016 | McBride et al. |
| 9,381,288 B2 | 7/2016 | Schenck et al. |
| 9,421,311 B2 | 8/2016 | Tanner et al. |
| 9,446,179 B2 | 9/2016 | Keenan et al. |
| 9,669,142 B2 | 6/2017 | Spanier et al. |
| 9,675,740 B2 | 6/2017 | Zeng et al. |
| 9,717,833 B2 | 8/2017 | McBride et al. |
| 9,770,543 B2 | 9/2017 | Tanner et al. |
| 9,814,814 B2 | 11/2017 | Corbett et al. |
| 9,872,947 B2 | 1/2018 | Keenan et al. |
| 9,872,948 B2 | 1/2018 | Siess |
| 9,895,476 B2 | 2/2018 | LaRose et al. |
| 9,907,890 B2 | 3/2018 | Muller |
| 9,956,332 B2 | 5/2018 | LaRose et al. |
| 9,962,475 B2 | 5/2018 | Campbell et al. |
| 9,964,115 B2 | 5/2018 | Scheckel |
| 10,029,037 B2 | 7/2018 | Muller et al. |
| 10,039,872 B2 | 8/2018 | Zeng et al. |
| 10,071,192 B2 | 9/2018 | Zeng |
| 10,086,121 B2 | 10/2018 | Fitzgerald et al. |
| 10,105,475 B2 | 10/2018 | Muller |
| 10,117,980 B2 | 11/2018 | Keenan et al. |
| 10,149,932 B2 | 12/2018 | McBride et al. |
| 10,215,187 B2 | 2/2019 | McBride et al. |
| 10,232,099 B2 | 3/2019 | Peters et al. |
| 10,251,985 B2 | 4/2019 | Larose et al. |
| 10,251,986 B2 | 4/2019 | Larose et al. |
| 10,279,095 B2 | 5/2019 | Aboul-Hosn et al. |
| 10,478,539 B2 | 11/2019 | Pfeffer et al. |
| 10,478,540 B2 | 11/2019 | Scheckel et al. |
| 10,525,178 B2 | 1/2020 | Zeng |
| 10,569,050 B1 | 2/2020 | Heesch |
| 10,576,192 B2 | 3/2020 | Muller et al. |
| 10,576,193 B2 | 3/2020 | Tanner et al. |
| 10,709,829 B2 | 7/2020 | Muller |
| 10,709,830 B2 | 7/2020 | Tanner et al. |
| 10,765,789 B2 | 9/2020 | Zeng et al. |
| 10,780,208 B2 | 9/2020 | Siess et al. |
| 10,786,610 B2 | 9/2020 | Zeng |
| 10,799,624 B2 | 10/2020 | Pfeffer et al. |
| 10,842,921 B2 | 11/2020 | Siess et al. |
| 10,864,308 B2 | 12/2020 | Muller et al. |
| 10,864,309 B2 | 12/2020 | McBride et al. |
| 10,874,783 B2 | 12/2020 | Pfeffer et al. |
| 10,894,115 B2 | 1/2021 | Pfeffer et al. |
| 10,918,774 B2 | 2/2021 | Stanfield et al. |
| 10,960,116 B2 | 3/2021 | Campbell et al. |
| 10,980,927 B2 | 4/2021 | Pfeffer et al. |
| 11,058,865 B2 | 7/2021 | Fitzgerald et al. |
| 11,123,539 B2 | 9/2021 | Pfeffer et al. |
| 11,129,978 B2 | 9/2021 | Pfeffer et al. |
| 11,167,124 B2 | 11/2021 | Pfeffer et al. |
| 11,229,786 B2 | 1/2022 | Zeng et al. |
| 11,235,138 B2 | 2/2022 | Gross-Hardt et al. |
| 11,253,693 B2 | 2/2022 | Pfeffer et al. |
| 11,260,213 B2 | 3/2022 | Zeng et al. |
| 11,273,301 B2 | 3/2022 | Pfeffer et al. |
| 11,285,309 B2 | 3/2022 | Tuval et al. |
| 11,305,105 B2 | 4/2022 | Corbett et al. |
| 11,311,712 B2 | 4/2022 | Zeng et al. |
| 11,338,124 B2 | 5/2022 | Pfeffer et al. |
| 11,357,967 B2 | 6/2022 | Zeng et al. |
| 11,400,276 B2 | 8/2022 | Chopra et al. |
| 11,497,896 B2 | 11/2022 | Tanner et al. |
| 11,517,736 B2 | 12/2022 | Earles et al. |
| 11,583,659 B2 | 2/2023 | Pfeffer et al. |
| D980,971 S | 3/2023 | Zarins et al. |
| D980,972 S | 3/2023 | Zarins et al. |
| 11,628,294 B2 | 4/2023 | Chopra et al. |
| 11,708,833 B2 | 7/2023 | McBride et al. |
| 11,754,075 B2 | 9/2023 | Schuelke et al. |
| 11,786,700 B2 | 10/2023 | Pfeffer et al. |
| 2003/0187322 A1 | 10/2003 | Siess |
| 2006/0161095 A1 | 7/2006 | Aboul-Hosn et al. |
| 2008/0103591 A1 | 5/2008 | Siess |
| 2008/0114339 A1 | 5/2008 | McBride et al. |
| 2009/0060743 A1 | 3/2009 | McBride et al. |
| 2009/0171137 A1 | 7/2009 | Farnan et al. |
| 2013/0303831 A1 | 11/2013 | Evans |
| 2017/0296725 A1 | 10/2017 | Peters et al. |
| 2018/0110908 A1 | 4/2018 | Larose |
| 2018/0303990 A1 | 10/2018 | Siess et al. |
| 2018/0311423 A1 | 11/2018 | Zeng et al. |
| 2019/0344001 A1 | 11/2019 | Salahieh et al. |
| 2019/0351180 A1* | 11/2019 | Ryu .................. A61B 34/20 |
| 2020/0330664 A1* | 10/2020 | Ship .................. A61M 60/135 |
| 2021/0015982 A1 | 1/2021 | Kerkhoffs et al. |
| 2021/0038785 A1 | 2/2021 | Siess et al. |
| 2021/0038791 A1 | 2/2021 | Tuval et al. |
| 2021/0106810 A1 | 4/2021 | Pfeffer et al. |
| 2022/0134082 A1 | 5/2022 | Pfeffer et al. |
| 2022/0184372 A1 | 6/2022 | Tuval et al. |

OTHER PUBLICATIONS

International Search Report and Written Opinion for International Application No. PCT/US2022/024782 dated Jul. 28, 2022 (14 pages).

\* cited by examiner

FLEXIBLE TIP FOR TRANSVALVULAR CIRCULATORY SUPPORT DEVICE

CROSS REFERENCE TO RELATED APPLICATION

This application claims priority to Provisional Application No. 63/174,810, filed Apr. 14, 2021, which is herein incorporated by reference in its entirety.

TECHNICAL FIELD

The present disclosure relates to percutaneous circulatory support devices. More specifically, the disclosure relates to flexible tips for use in percutaneous circulatory support devices.

BACKGROUND

Percutaneous circulatory support devices such as blood pumps can provide transient support for hours or months of use in patients whose heart function or cardiac output is compromised. Such devices are delivered percutaneously from the femoral artery, retrograde through the descending aorta, over the aortic arch, through the ascending aorta across the aortic valve, and into the left ventricle. Several issues may complicate the delivery and operation of blood pumps within the heart, including chordae tendineae entanglement, difficulty with guidewire movement, interference with lateral left ventricle contraction, generation of premature ventricular contractions, trauma to cardiac tissue, and oscillation of the blood pump resulting in decreased performance of the blood pump.

SUMMARY

In Example 1, a blood pump comprises a flexible distal tip comprising a distal end segment, an intermediate segment, and a proximal segment. The intermediate segment has a curved shape, and the distal end segment has a curved shape that overlaps with the intermediate segment but not the proximal segment.

In Example 2, the blood pump of Example 1, wherein the proximal segment has a first hardness, the distal end segment has a second hardness, and the first hardness is greater than the second hardness.

In Example 3, the blood pump of any of Examples 1-2, wherein the flexible distal tip comprises a polymer.

In Example 4, the blood pump of any of Examples 1-3, wherein the proximal segment has a first wall thickness and the distal end segment has a second wall thickness.

In Example 5, the blood pump of any of Examples 1-4, wherein the proximal segment is comprised of a first material and the distal end segment is comprised of a second material.

In Example 6, the blood pump of any of Examples 1-5, further comprising a cannula and a can element. The can element couples the flexible distal tip to the cannula.

In Example 7, the blood pump of Example 6, wherein the can element comprises a distal component and a proximal component.

In Example 8, the blood pump of any of Examples 6-7, wherein the cannula comprises one or more tines, and wherein the one or more tines are coupled to the proximal component of the can element with an adhesive.

In Example 9, the blood pump of any of Examples 6-8, wherein the distal tip is coupled to the can element with an adhesive.

In Example 10, a blood pump comprises a cannula and a flexible distal tip forming a loop. The loop has a proximal end coupled to the cannula, a distal end, and a lumen extending between the proximal end and the distal end.

In Example 11, the blood pump of Example 10, wherein the lumen allows for passage of a guidewire from the proximal end of the loop to the distal end of the loop.

In Example 12, the blood pump of any of Examples 10-11, wherein the lumen extends from the proximal end of the loop to the distal end of the loop via a guidewire support lumen connecting the proximal end and the distal end of the loop.

In Example 13, the blood pump of any of Examples 10-12, wherein the flexible distal tip comprises a polymer.

In Example 14, the blood pump of any of Examples 10-13, wherein the flexible distal tip has a length of approximately 20 mm and a width of approximately 10 mm.

In Example 15, the blood pump of any of Examples 10-14, wherein the flexible distal tip further comprises a secondary loop. The loop is joined to the secondary loop such that the loop is offset from the secondary loop by 90 degrees.

In Example 16, a blood pump comprises a flexible distal tip comprising a distal end segment, an intermediate segment, and a proximal segment. The proximal segment has a relatively straight shape, the intermediate segment has a curved shape, and the distal end segment has a curved shape that overlaps with the intermediate segment but not the proximal segment.

In Example 17, the blood pump of Example 16, wherein the proximal segment has a first hardness, the distal end segment has a second hardness, and the first hardness is greater than the second hardness.

In Example 18, the blood pump of Example 16, wherein the flexible distal tip comprises a polymer.

In Example 19, the blood pump of Example 16, wherein the proximal segment has a first wall thickness and the distal end segment has a second wall thickness.

In Example 20, the blood pump of Example 16, wherein the proximal segment is comprised of a first material and the distal end segment is comprised of a second material.

In Example 21, the blood pump of Example 16, further comprising a cannula and a can element. The can element couples the flexible distal tip to the cannula.

In Example 22, the blood pump of Example 21, wherein the can element comprises a distal component and a proximal component.

In Example 23, the blood pump of Example 21, wherein the cannula comprises one or more tines, and wherein the one or more tines are coupled to the proximal component of the can element with an adhesive.

In Example 24, the blood pump of Example 21, wherein the distal tip is coupled to the can element with an adhesive.

In Example 25, a blood pump comprises a cannula and a flexible distal tip forming a loop. The loop has a proximal end coupled to the cannula, a distal end, and a lumen extending between the proximal end and the distal end.

In Example 26, the blood pump of Example 25, wherein the lumen allows for passage of a guidewire from the proximal end of the loop to the distal end of the loop.

In Example 27, the blood pump of Example 26, wherein the lumen extends from the proximal end of the loop to the distal end of the loop via a curved segment of the loop.

In Example 28, the blood pump of Example 26, wherein the lumen extends from the proximal end of the loop to the distal end of the loop via a guidewire support lumen connecting the proximal end and the distal end of the loop.

In Example 29, the blood pump of Example 25, wherein the flexible distal tip comprises a polymer.

In Example 30, the blood pump of Example 25, wherein the flexible distal tip has a length of approximately 20 mm and a width of approximately 10 mm.

In Example 31, the blood pump of Example 25, wherein the flexible distal tip further comprises a secondary loop. The loop is joined to the secondary loop such that the loop is offset from the secondary loop by 90 degrees.

In Example 32, the blood pump of Example 31, wherein the secondary loop comprises a polymer.

In Example 33, a method of assembling a blood pump comprises coupling one or more tines to a cannula, coupling the one or more tines to a proximal component of a can element, coupling a distal component of a can element to the proximal component of the can element, and coupling a flexible distal tip to the distal component of the can element In Example 34, the blood pump of Example 33, further comprising coupling the distal tip to the can element using an adhesive.

In Example 35, the blood pump of Example 33, further comprising coupling the distal component to the proximal component using an adhesive.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
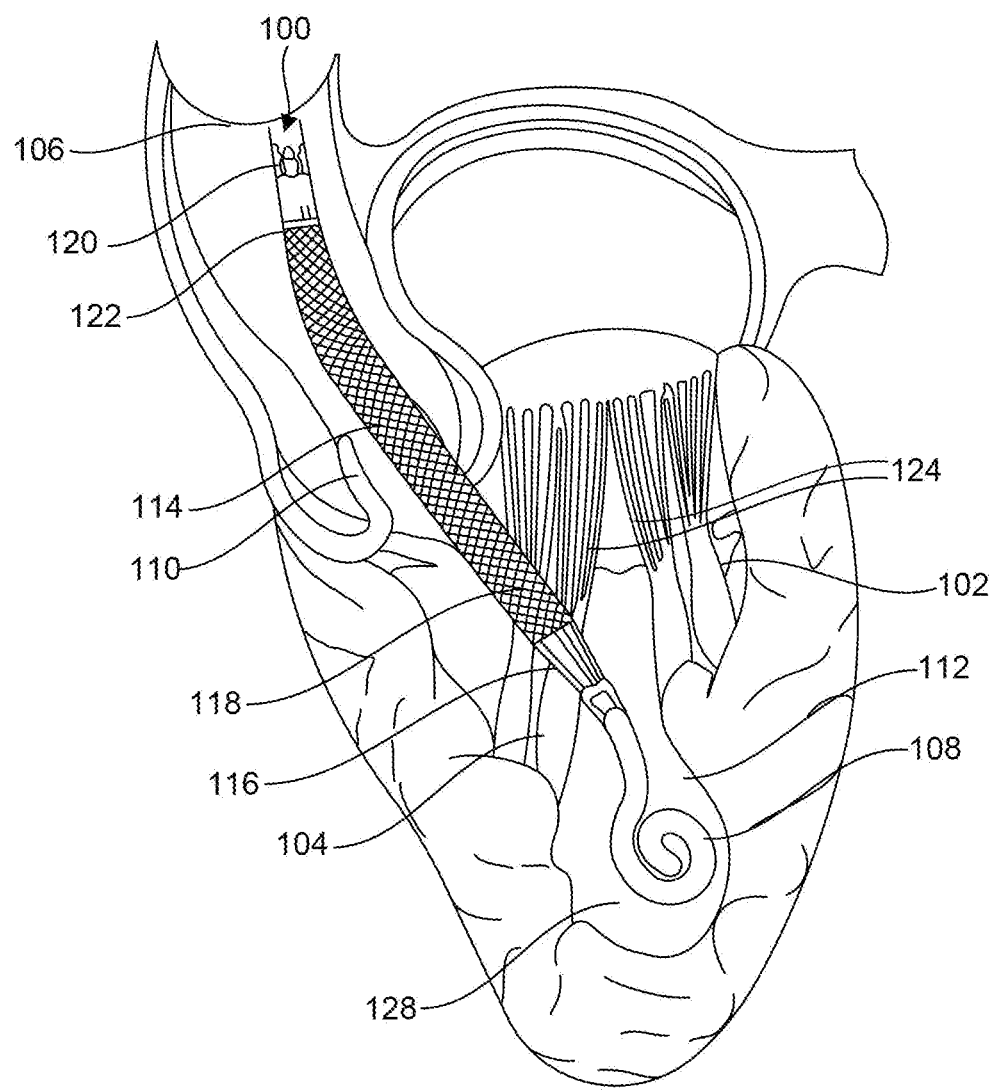
FIG. 1 depicts a portion of an illustrative percutaneous mechanical circulatory support device (also referred to herein, interchangeably, as a "blood pump"), and its relative position in a heart, in accordance with embodiments of the subject matter disclosed herein.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 depicts a portion of an illustrative percutaneous mechanical circulatory support device (also referred to herein, interchangeably, as a "blood pump"), and its relative position in a human heart, in accordance with embodiments of the subject matter disclosed herein. Blood pump 100 may be delivered percutaneously using a guidewire (not shown), passing from the femoral artery (not shown), retrograde through the descending aorta (not shown), over the aortic arch (not shown), through the ascending aorta 106, past the aortic valve 110, and into the left ventricle 112. Blood pump 100 includes a cannula 114 and a flexible distal tip 108. The cannula 114 may also have a flexible construction to facilitate delivery of the blood pump 100. The cannula 114 includes one or more blood inlets 116 located on a distal section 118 of the cannula 114, and one or more blood outlets 120 which are located within the pump housing 122.

During delivery, the blood pump 100, and in particular the distal tip 108, may contact structures within the heart, such as the aortic valve 110, one or more chordae tendineae 124 emanating from the posterior papillary muscle 102 or anterior papillary muscle 104. During operation, the blood pump 100 is positioned within the heart such that the one or more blood inlets 116 is positioned in the left ventricle 112 and the one or more blood outlets 120 is positioned in the aorta 106, as show in FIG. 1. The blood pump 100 may be positioned such that the distal tip 108 contacts the left ventricular wall 126, for example, in the location of the apex 128 of the left ventricle 112.

Figure 2A:
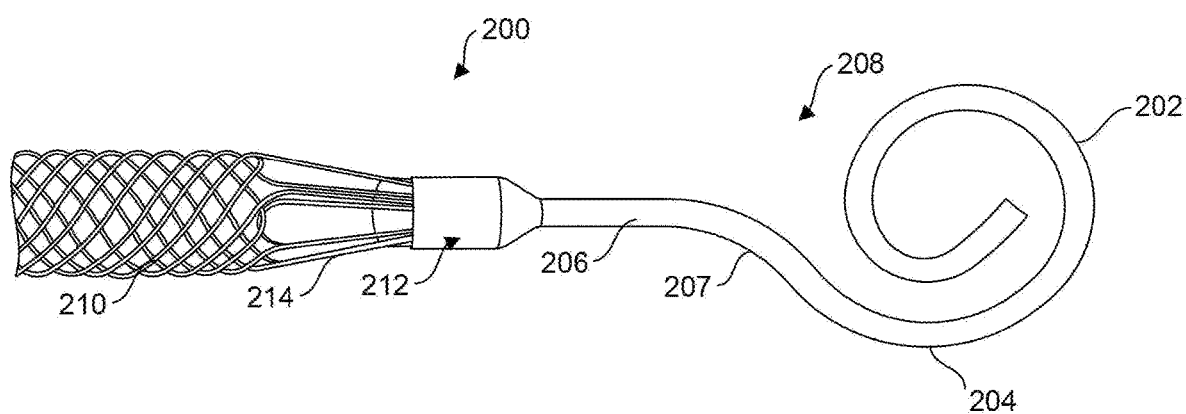
FIG. 2A depicts a side view of a portion of an embodiment of an illustrative percutaneous mechanical circulatory support device, in accordance with embodiments of the subject matter disclosed herein.

FIG. 2A depicts a side view of a portion of an embodiment of an illustrative percutaneous mechanical circulatory support device, in accordance with embodiments of the subject matter disclosed herein. As shown, a blood pump 200 includes a cannula 210, a can element 212, one or more tines 214 (described in more details with respect to FIG. 2B), and a flexible distal tip 208. The distal tip 208 includes a distal end segment 202, an intermediate segment 204, and a proximal segment 206. The distal tip 208 also may include a lumen (not shown) to facilitate passage of a guidewire (not shown). The proximal segment 206 has a relatively straight shape, the intermediate segment 204 has a curved shape, and the distal end segment 202 has a curved shape that overlaps with the intermediate segment 204 but not the proximal segment 206. In some embodiments, and as shown in FIG. 2A, a bend segment 207 may extend and form a gradually curved transition between proximal segment 206 and intermediate segment 204. A guidewire (not shown) may extend through the cannula 210, can element 212, and distal tip 208 via the lumen of the distal tip 208. In some embodiments, the guidewire diameter may be approximately 0.018 inches. In order to accommodate the guidewire, the inner diameter of the lumen of the distal tip 208 may be from 0.030 to 0.050 inches, and the outer diameter of the lumen of the distal tip 208 may be from 0.050 to 0.100 inches. In certain embodiments, the inner diameter of the lumen of the distal tip 208 may be approximately 0.040 inches, and the outer diameter of the lumen of the distal tip 208 may be approximately 0.080 inches.

The distal tip 208 may be made of one or more materials, such as one or more polymers (i.e. Pebax, Pellethane), rubbers, plastics, or other materials known to a person skilled in the art that allow the distal tip 208 to be flexible, relatively soft, and/or collapsible. In some embodiments, a preferred material for the distal tip 208 is Pebax. In certain embodiments, the distal tip 208 may be made of a flexible metal material (e.g., Nitinol, Elgiloy, or another metal material with desirable properties). Distal tip 208 may also include features, such as slots or other structures to improve flexibility, collapsibility, performance, durability, or other desirable characteristics. In some embodiments, the distal tip 208 may be slotted and made of Nitinol that may be heat set to various shapes. In certain embodiments, and in particular when the distal tip 208 has a tighter radius (i.e. smaller overall diameter) or when the distal tip 208 includes long, curved lengths, the inner diameter of the distal tip 208 may be lined with a lubricious material or liner to facilitate passage of the guidewire through the lumen of the distal tip 208.

Introduction of a guidewire (not shown) into the distal tip 208 may expand or straighten the curved shapes of the intermediate segment 204 and distal end segment 202 of the distal tip 208. In certain instances, when the guidewire is retracted, the curved shape of the intermediate segment 204 and distal end segment 202 may retract to their original shape. In particular, choice of the shape and material of the distal tip 208 may allow for the tip 208 to unfurl during extraction of the blood pump 200 and disengage from the one or more chordae or other structures without tearing or damaging these structures. In other instances, depending on the material used for the flexible distal tip 208, when the guidewire is retracted, the curved shape of the intermediate segment 204 and distal end segment 202 may not retract to their original shape, and may remain expanded or straightened.

The proximal segment 206 of the distal tip 208 is constructed to have moderate stiffness, so that it may act as a dampener absorbing forces acting on the distal tip 208 and blood pump 200. Moderate stiffness for the proximal segment 206 is also beneficial so that the distal tip 208 may provide axial strength, which is advantageous for positioning and supporting the cannula 210 in the left ventricle. The appropriate stiffness of proximal segment 206 may be achieved by constructing the proximal segment 206 of one or more materials of appropriate hardness, by the inclusion of structures, such as reinforcement structures or slots, within the proximal segment 206 to achieve the appropriate stiffness, by combining materials and structures to achieve the appropriate stiffness, or by using other techniques known to one of ordinary skill in the art. In some advantageous embodiments, the bend segment 207 may also facilitate dampening and absorbing axial forces acting on the distal tip 208, and be constructed of similar materials as the proximal segment 206.

The intermediate segment 204 of the distal tip 208 is constructed to have a stiffness less than the stiffness of the proximal segment 206. Such a stiffness for the intermediate segment 204 is beneficial so that the intermediate segment 204 does not cause trauma or damage when contacting tissue, yet provides adequate structural strength for positioning and supporting of the cannula 210 in the left ventricle while also being capable of absorbing forces acting on the distal tip 208. The appropriate stiffness of intermediate segment 204 may be achieved by constructing the intermediate segment 204 of one or more materials of appropriate hardness, by the inclusion of structures, such as reinforcement structures or slots, within the intermediate segment 204 to achieve the appropriate stiffness, by combining materials and structures to achieve the appropriate stiffness, or by using other techniques known to one of ordinary skill in the art. In general, the intermediate segment 204 may be constructed of materials that have a hardness less than the hardness of the materials forming the proximal segment 206, as measured, for example, by a durometer.

The distal end segment 202 of the distal tip 208 is constructed to have a stiffness less than the stiffness of the intermediate segment 204. Such a stiffness for the distal end segment 202 is beneficial so that distal end segment 202 does not cause trauma or damage when contacting tissue, yet provides adequate structural strength for positioning and supporting of the cannula 210 in the left ventricle while also being capable of absorbing forces acting on the distal tip 208. The appropriate stiffness of the distal end segment 202 may be achieved by constructing the distal end segment 202 of one or more materials of appropriate hardness, by the inclusion of structures, such as reinforcement structures or slots, within the distal end segment 202 to achieve the appropriate stiffness, by combining materials and structures to achieve the appropriate stiffness, or by using other techniques known to one of ordinary skill in the art. In general, the distal end segment 202 may be constructed of materials that have a hardness less than the hardness of the materials forming intermediate segment 204, as measured, for example, by a durometer. In certain embodiments, based on the materials used for the reinforcement structures, the inclusion of the structures may aid in the visualization for the distal tip 208 under fluoroscopy.

As described above, the distal tip 208 has a proximal segment 206 and a distal end segment 202, and the hardness of the proximal segment 206 may be greater than the hardness of the distal end segment 202. In certain embodiments, the hardness transition may occur in discrete steps along the length of the distal tip 208. In some embodiments, the hardness transition may be gradual or continuous along the length of the distal tip 208. In other embodiments, the hardness transition may be a combination of discrete steps and continuous segments. The decrease in hardness from the proximal segment 206 to the distal end segment 202 of the distal tip 208 may be achieved through a variety of ways, such as decreasing wall thickness of the distal tip 208 from the proximal segment 206 to the distal end segment 202, decreasing hardness of material along the length of distal tip 208 without using discrete segments (e.g., intermittent layer co-extrusion), changing the pattern or construction of the walls of the distal tip 208 along the length of distal tip 208, changing the pattern or construction of internal support structures within the walls of the distal tip 208 along the length of the distal tip 208, heat treating the distal tip 208 or portions thereof to change the material properties of the distal tip 208 or portions thereof, or by any other method known by a person of ordinary skill in the art.

There are numerous advantages to the distal tip 208 described in relation to FIG. 2A. Constructing the distal tip 208 to be flexible, relatively soft, and/or collapsible helps prevent the distal tip 208 from causing trauma or damage to vascular or cardiac tissues and structures during delivery or operation of the blood pump 200, and may assist in delivery of the blood pump through the vascular and cardiac structures. For example, the curved shapes and material properties of the intermediate segment 204 and the distal end segment 202 protect against potential entanglement of the distal tip 208 in cardiac structures, such as the one or more set of chordae tendineae 124 emanating from the posterior papillary muscle or the anterior papillary muscle (shown in FIG. 1), during delivery of the blood pump 200. Similarly, the overlapping arrangement of the intermediate segment 204 and the distal end segment 202 avoids potential entanglement of the distal tip 208 with cardiac structures when introducing the blood pump 200 into the heart. A flexible and/or relatively soft distal tip 208 also helps prevent the guidewire from damaging or causing trauma to vascular or cardiac structures. In addition, a flexible and/or collapsible distal tip 208 facilitates navigation of the blood pump 200 through vascular and cardiac structures. For example, the curved shapes and material properties of the intermediate segment 204 and the distal end segment 202 allow the distal tip 208 to unfurl during extraction of the blood pump 200, permitting the distal tip 208 to pass through or disengage from the chordae without tearing or damaging these structures. Also, a flexible, relatively soft, and/or collapsible distal tip 208 also helps maintain the blood pump 200 in proper position within the heart by absorbing or dampening forces, such as blood flow or ventricular wall contact, acting on the blood pump 200 when the distal tip 208 is positioned against a wall of the left ventricle. If the cannula 210 is constructed to be flexible, there may be movement or oscillation of the blood pump 200 within the heart due to blood flow and contraction of the heart. The flexible, relatively soft, and/or collapsible distal tip 208 also accounts for and minimizes resistance to lateral contraction forces acting on the tip 208 during contraction of the left ventricle. The distal tip 208 as shown in FIG. 2A significantly reduces such movement or oscillation by supporting the distal tip 208 of the blood pump 200 against a wall of the left ventricle, thereby stabilizing the overall blood pump 200. Such stabilization of the blood pump 200 may increase efficiency, performance, and/or longevity of the blood pump 200.

Figure 2B:
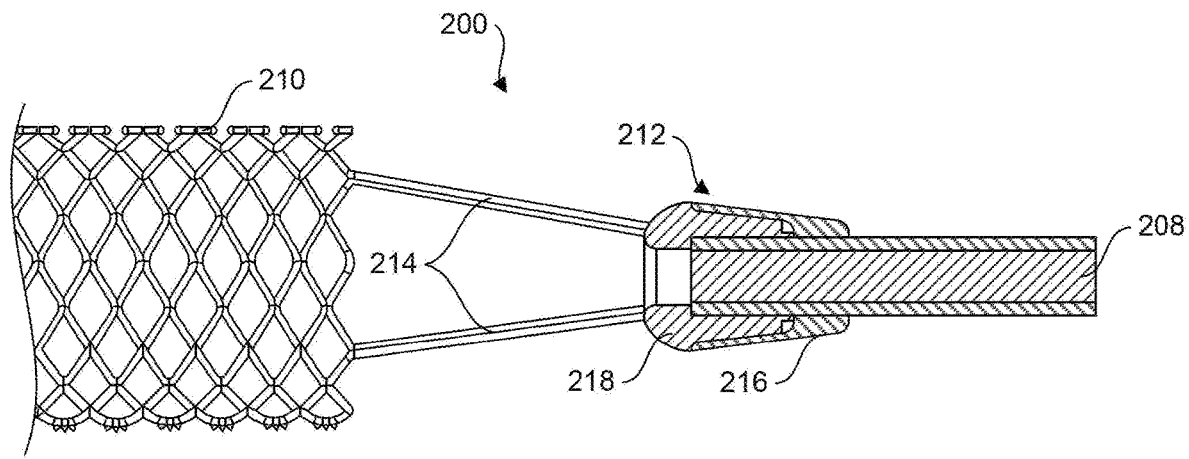
FIG. 2B depicts an enlarged view of a portion of the embodiment of an illustrative percutaneous mechanical circulatory support device shown in FIG. 2A, in accordance with embodiments of the subject matter disclosed herein.

FIG. 2B depicts an enlarged view of a portion of the embodiment of an illustrative percutaneous mechanical circulatory support device shown in FIG. 2A. As shown, the blood pump 200 includes a can element 212, a cannula 210, and a flexible distal tip 208 (partially shown). The can element 212 includes a distal component 216 and a proximal component 218, and may be used to couple the distal tip 208 to the cannula 210. The cannula 210 further includes one or more tines 214. The one or more tines 214 may be coupled to the proximal component 218 of the can element 212 using an adhesive or mechanical coupling, preferably prior to the distal component 216 of the can element 212 being attached to the proximal component 218 of the can element 212. Such a construction provides, for example, a direct line of sight available when curing an adhesive. The distal component 216 of the can element 212 may then be slid over the proximal component 218 of the can element 212 and attached to the proximal component 218 of the can element 212. The distal component 216 may be mechanically coupled to the proximal component 218 of the can element 212, or coupled with an adhesive. The distal tip 208 may be coupled to the proximal component 218 of the can element 212 using an adhesive or mechanical coupling, either before or after the distal component 216 of the can element 212 is attached to the proximal component 218 of the can element 212. The distal tip 208 may also be coupled to the distal component 216, or the proximal component 218 and distal component 216, of the can element 212.

In some embodiments, the can element 212 may be composed of stainless steel and the distal tip 208 may be composed of Nitinol. In such embodiments, the distal tip 208 may be joined to the can element 212 using an adhesive, as the use of an adhesive is a preferred method for joining dissimilar materials, and laser or other types of welding are not preferred for joining such materials. One preferred example of suitable adhesive for joining the proximal component 218 and distal component 216 is ultraviolet adhesive. The use of ultraviolet adhesives results in an average bond strength of 6 pounds per foot. Laser or other types of welding may be used in other embodiments, and may be preferable, for joining similar metals or other materials. For example, in other embodiments, the distal tip 208 and can element 212 may be made of similar metals, and may be joined together using laser welding, or other techniques known by a person of ordinary skill in the art. Alternative methods and materials known to one of ordinary skill in the art for securing the tines 214 to the cannula 210, the distal tip 208 to the proximal component 218 and/or distal component 216 of the can element 212, or the proximal component 218 and distal component 216 of the can element 212, may be used. Examples of alternative methods include the use of welding, soldering, brazing, crimping, threaded connection, and other types of mechanical couplings. In certain embodiments, the use of mechanical couplings may be preferred to achieve consistency in strength and durability.

The above-described can element 212 provides several advantages. For example, inclusion of the can element 212 provides mass at the distal section of the cannula 210, which contributes to the overall cannula and blood pump stability. Constructing the can element 212 of a highly polished stainless-steel material may also minimize thrombus formation on the blood pump. The overall design of the can element 212 and distal tip 208 also provides a seamless transition from the proximal component 218 of the can element 212 into the distal tip 208, helping to prevent a guidewire (not shown here) from catching on the proximal end of the distal tip 208 or components of the can element 212. The above-described can element 212 is compatible with alternative embodiments of distal tips discussed below with respect to FIGS. 3A-30 and FIG. 4.

Figure 3A:
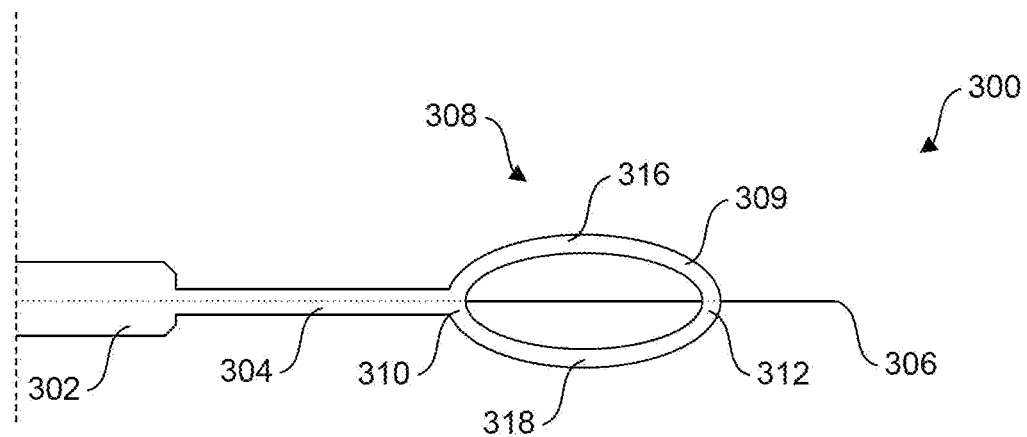
FIG. 3A depicts a side view of a portion of an embodiment of an illustrative percutaneous mechanical circulatory support device, in accordance with embodiments of the subject matter disclosed herein.

FIG. 3A depicts a side view of a portion of an alternative embodiment of an illustrative percutaneous mechanical circulatory support device, in accordance with embodiments of the subject matter disclosed herein. As shown, a partial view of a blood pump 300 includes a can element 302, a center lumen 304, and a flexible distal tip 308. The distal tip 308 forms a closed loop 309, which includes a proximal end 310 and a distal end 312. The closed loop shape allows for the distal tip 308 to perform its beneficial functions (e.g., stabilization of the blood pump, facilitating guidewire movement, reducing the potential for chordae entanglement, etc.). In embodiments, the inner diameter of the center lumen 304 may be from 0.030 to 0.050 inches, and the outer diameter of the center lumen 304 may be from 0.050 to 0.100 inches. In some embodiments, the inner diameter of the center lumen 304 may be approximately 0.04 inches, and the outer diameter of the center lumen 304 may be approximately 0.08 inches. In some embodiments, the length of the closed loop 309 may be around 10-40 mm, and the width of the closed loop 309 may be around 5-20 mm. In some embodiments, the length of the closed loop 309 may be approximately 20 mm, and the width of the closed loop 309 may be approximately 10 mm.

Figure 3B:
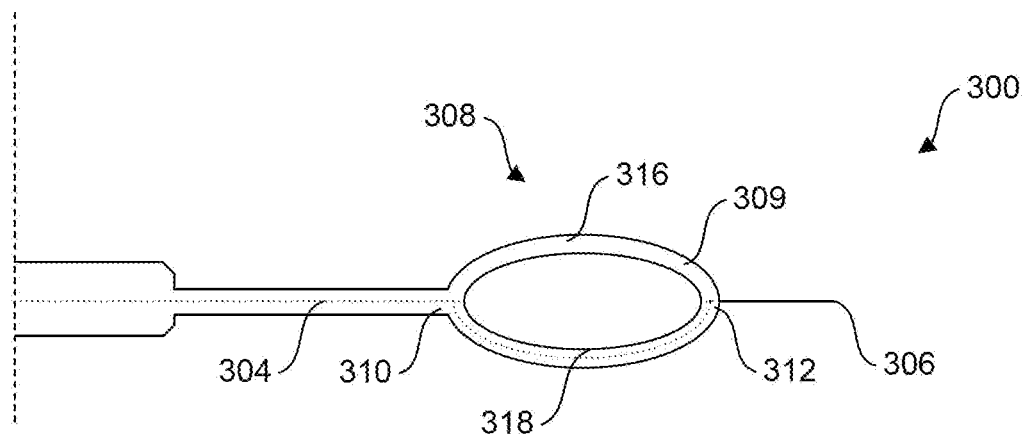
FIG. 3B depicts a side view of a portion of an embodiment of an illustrative percutaneous mechanical circulatory support device, in accordance with embodiments of the subject matter disclosed herein.
Figure 3C:
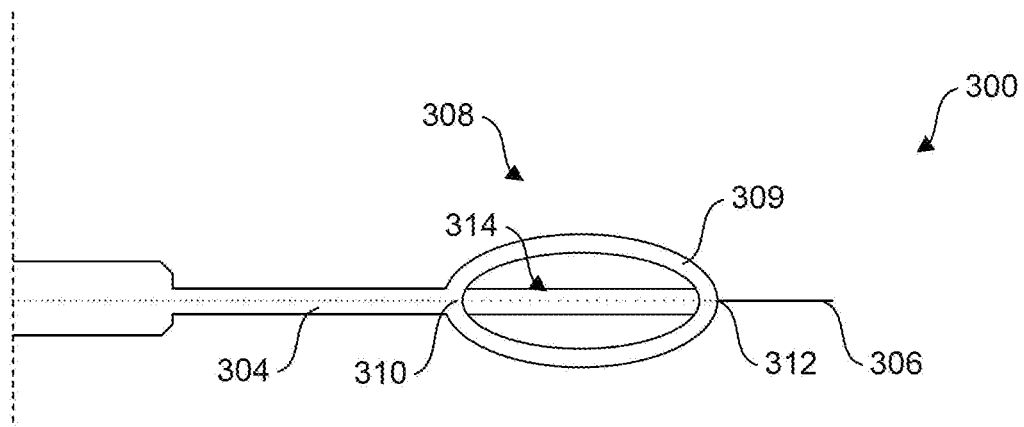
FIG. 3C depicts a side view of a portion of an embodiment of an illustrative percutaneous mechanical circulatory support device, in accordance with embodiments of the subject matter disclosed herein.

In the embodiment in FIG. 3A, the center lumen 304 does not extend through curved portions 316, 318 of the closed loop 309; instead, as shown, the guidewire 306 passes through the center lumen 304, and then across the closed loop 309 between the proximal end 310 and distal end 312 of the distal tip 308. Alternatively, as shown in FIG. 3B, the center lumen 304 may extend from the proximal end 310 of the loop 309 to the distal end 312 of the loop 309 via one of the curved portions 316 or 318 of the closed loop 309, such that guidewire 306 may pass from the proximal end 310, through one of curved portions 316, 318, to distal end 312 of the distal tip 308. In another alternative, as shown in FIG. 3C, the center lumen 304 may extend from the proximal end 310 of the loop 309 to the distal end 312 of the loop 309 via a guidewire support lumen 314, which directly connects the proximal end 310 and the distal end 312 of the loop 309. In other respects, the distal tip 308 shown in FIGS. 3A, 3B, and 3C may be constructed of the materials and according to the dimensions of the embodiment described above with respect to FIG. 2A. For example, the inner diameter of the distal tip 308 may be lined with a lubricious material or liner to facilitate passage of a guidewire through the lumen of the distal tip 308.

Figure 4:
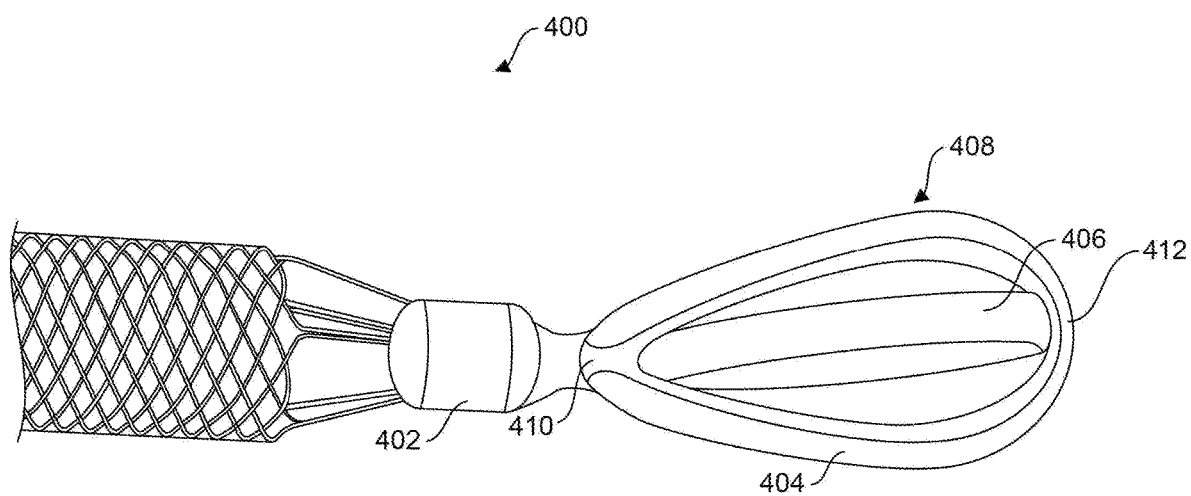
FIG. 4 depicts a side view of a portion of an alternative embodiment of an illustrative percutaneous mechanical circulatory support device, in accordance with embodiments of the subject matter disclosed herein.

FIG. 4 depicts a side view of a portion of an alternative embodiment of an illustrative percutaneous mechanical circulatory support device, in accordance with embodiments of the subject matter disclosed herein. As shown, a partial view of a blood pump 400 includes a can element 402 and a flexible distal tip 408. The distal tip 408 includes a first loop 404 and a second loop 406. The first loop 404 is joined to the second loop 406 such that the first loop 404 is offset from the second loop 406 by 90 degrees, forming a 3-dimensional "whisk" shape. This "whisk" shaped distal tip 408 allows for multiple contact points in the left ventricle, which reduces the contact pressure on the ventricle wall at any one point of contact, thereby minimizing the risk of tissue damage. The distal tip 408 shown in FIG. 4 may be constructed of the materials and according to the dimensions of the embodiment described above with respect to FIG. 2A, including, for example, the use of a lubricious material or liner to facilitate passage of a guidewire through the lumen of the distal tip 308.

In some embodiments, a guidewire (not shown) may pass through the proximal portion 410 and distal portion 412 of the distal tip 408 without overlapping with the first loop 404 or the second loop 406. Alternatively, a guidewire may extend through one of the curved portions of one of the loops 404, 406 in addition to the proximal portion 410 and distal portion 412 of the distal tip 408. Alternatively, in some embodiments, the distal tip 408 may include a guidewire support lumen (not shown, but similar to what is shown in FIG. 3C) extending across the loops 404, 406. In embodiments, the inner diameter of the guidewire support lumen may be from 0.030 to 0.050 inches, and the outer diameter of the guidewire support lumen may be from 0.050 to 0.100 inches. In some embodiments, the inner diameter of the guidewire support lumen may be approximately 0.04 inches, and the outer diameter of the guidewire support lumen may be approximately 0.08 inches.

Various modifications and additions can be made to the exemplary embodiments discussed without departing from the scope of the present invention. For example, while the embodiments described above refer to particular features, the scope of this invention also includes embodiments having different, combinations of features and embodiments that do not include all of the described features. Accordingly, the scope of the present invention is intended to embrace all such alternatives, modifications, and variations as fall within the scope of the claims, together with all equivalents thereof.

The invention claimed is:

1. A blood pump, comprising:
   a flexible distal tip comprising:
   a distal end segment having a first end and a second end;
   an intermediate segment having a first end and a second end; and
   a proximal segment having a first end and a second end;
   wherein the distal end of the proximal segment adjoins the proximal end of the intermediate segment at a first location, and the distal end of the intermediate segment adjoins the proximal end of the distal end segment at a second location; and
   wherein the proximal segment has a relatively straight shape from the proximal end of the proximal segment to the distal end of the proximal segment, the intermediate segment has a curved shape from the proximal end of the intermediate segment to the distal end of the intermediate segment, and the distal end segment has a curved shape that overlaps with the intermediate segment but does not extend proximal of the distal end of the proximal segment.

2. The blood pump of claim 1:
   wherein the proximal segment has a first hardness, and the distal end segment has a second hardness, and
   wherein the first hardness is greater than the second hardness.

3. The blood pump of claim 1, wherein the flexible distal tip comprises a polymer.

4. The blood pump of claim 1, wherein the proximal segment has a first wall thickness and the distal end segment has a second wall thickness.

5. The blood pump of claim 1, wherein the proximal segment is comprised of a first material and the distal end segment is comprised of a second material.

6. The blood pump of claim 1, further comprising:
   a cannula; and a can element;
   wherein the can element couples the flexible distal tip to the cannula.

7. The blood pump of claim 6, wherein the can element comprises a distal component and a proximal component.

8. The blood pump of claim 6, wherein the cannula comprises one or more tines, and wherein the one or more tines are coupled to the proximal component of the can element with an adhesive.

9. The blood pump of claim 6, wherein the distal tip is coupled to the can element with an adhesive.

10. A method of assembling a blood pump, comprising:
    coupling one or more tines to a cannula;
    coupling the one or more tines to a proximal component of a can element;
    coupling a distal component of a can element to the proximal component of the can element; and
    coupling a flexible distal tip to the distal component of the can element;
    wherein the distal component of the can element extends distally past a distal end of the tines.

11. The method of claim 10, further comprising:
    coupling the distal tip to the can element using an adhesive.

12. The method of claim 10, further comprising:
    coupling the distal component to the proximal component using an adhesive.

13. A blood pump, comprising:
    a flexible distal tip comprising:
    a distal end segment having a first end and a second end;

an intermediate segment having a first end and a second end; and a proximal segment having a first end and a second end;

wherein the distal end of the proximal segment adjoins the proximal end of the intermediate segment at a first location, and the distal end of the intermediate segment adjoins the proximal end of the distal end segment at a second location;

wherein the proximal segment has a relatively straight shape defining a longitudinal axis, the intermediate segment has a curved shape, and the distal end segment has a curved shape that overlaps with the intermediate segment but does not extend proximal of the distal end of the proximal segment, and wherein the intermediate segment curves in a first direction away from the longitudinal axis, and the distal end segment curves in a second direction to intersect with the longitudinal axis.

14. The blood pump of claim 13:

wherein the proximal segment has a first hardness, and the distal end segment has a second hardness, and wherein the first hardness is greater than the second hardness.

15. The blood pump of claim 13, wherein the flexible distal tip comprises a polymer.

16. The blood pump of claim 13, wherein the proximal segment has a first wall thickness and the distal end segment has a second wall thickness.

17. The blood pump of claim 13, wherein the proximal segment is comprised of a first material and the distal end segment is comprised of a second material.

18. The blood pump of claim 13, further comprising:

a cannula; and a can element;

wherein the can element couples the flexible distal tip to the cannula.

19. The blood pump of claim 18, wherein the can element comprises a distal component and a proximal component.

20. The blood pump of claim 18, wherein the cannula comprises one or more tines, and wherein the one or more tines are coupled to the proximal component of the can element with an adhesive.

* * * * *